United States Patent
Ruch et al.

(10) Patent No.: US 11,725,966 B2
(45) Date of Patent: Aug. 15, 2023

(54) MULTI-STAGE IRREVERSIBLE SENSOR COUPLING

(71) Applicant: Rosemount Inc., Shakopee, MN (US)

(72) Inventors: Tyrel L. Ruch, Saint Paul, MN (US); John W. Simon, Burnsville, MN (US)

(73) Assignee: ROSEMOUNT INC., Shakopee, MN (US)

( * ) Notice: Subject to any disclaimer, the term of this patent is extended or adjusted under 35 U.S.C. 154(b) by 224 days.

(21) Appl. No.: 17/025,017

(22) Filed: Sep. 18, 2020

(65) Prior Publication Data

US 2022/0091085 A1    Mar. 24, 2022

(51) Int. Cl.
  *G01D 11/24*  (2006.01)
  *G01N 33/00*  (2006.01)

(52) U.S. Cl.
  CPC ....... *G01D 11/245* (2013.01); *G01N 33/0009* (2013.01); *G01N 33/0075* (2013.01)

(58) Field of Classification Search
  CPC ...... G01D 11/24; G01D 11/245; G01D 11/00; F16B 7/10; F16B 7/105; F16B 7/14; F16B 7/1463; F16B 17/00; F16B 21/00; F16B 2200/50
  See application file for complete search history.

(56) References Cited

U.S. PATENT DOCUMENTS

| | | |
|---|---|---|
| 4,046,451 A | 9/1977 | Juds et al. |
| 4,359,255 A | 11/1982 | Gallusser et al. |
| 6,252,510 B1 | 6/2001 | Dungan |
| 6,670,887 B2 | 12/2003 | Dungan |
| 6,794,991 B2 | 9/2004 | Dungan |
| 7,089,778 B2 | 8/2006 | Rabenecker et al. |
| 7,345,590 B2 | 3/2008 | Nakano et al. |
| 7,633,963 B1 | 12/2009 | Anderson et al. |
| 8,358,105 B2 | 1/2013 | Barten et al. |
| 8,578,783 B2 | 11/2013 | Hedtke et al. |
| 8,640,560 B2 | 2/2014 | Burke |
| 2002/0013088 A1 | 1/2002 | Rodrigues et al. |

(Continued)

FOREIGN PATENT DOCUMENTS

| | | |
|---|---|---|
| CN | 103348057 A | 10/2013 |
| CN | 104067455 A | 9/2014 |

(Continued)

OTHER PUBLICATIONS

Search Report and Written Opinion dated Dec. 15, 2021 for International Patent Application No. PCT/US2021/048645, 11 pages.

*Primary Examiner* — Benjamin R Schmitt
(74) *Attorney, Agent, or Firm* — Christopher R. Christenson; Kelly, Holt & Christenson PLLC (57) ABSTRACT

A multi-stage irreversible sensor coupling is provided. A sensor body includes a sensor and has a sensor body wall and at least one sensor body engagement feature. A clip barrel is configured to slidably engage the sensor body and has at least one clip barrel engagement feature. A wedge clip is configured to slidably engage the clip barrel and has at least one wedge clip engagement feature that is configured to urge the at least one sensor body engagement feature into cooperative engagement with the at least one clip barrel engagement feature when the wedge clip, clip barrel, and sensor body are fully engaged together.

12 Claims, 7 Drawing Sheets

(56) References Cited

U.S. PATENT DOCUMENTS

| | | |
|---|---|---|
| 2002/0102884 A1 | 8/2002 | Pechstein et al. |
| 2004/0027912 A1 | 2/2004 | Bibbo et al. |
| 2004/0209507 A1 | 10/2004 | Starta et al. |
| 2006/0266097 A1 | 11/2006 | Eickhoff |
| 2007/0186630 A1* | 8/2007 | Skarpil ............... B29C 66/1122 73/114.25 |
| 2012/0240686 A1 | 9/2012 | Blomberg et al. |
| 2013/0319987 A1 | 12/2013 | Beistle et al. |
| 2015/0177206 A1 | 6/2015 | Basham et al. |
| 2015/0204830 A1 | 7/2015 | Arunachalam |
| 2018/0085696 A1 | 3/2018 | Morris et al. |

FOREIGN PATENT DOCUMENTS

| | | | |
|---|---|---|---|
| CN | 104769651 A | 7/2015 | |
| EP | PCT/EP2002/000369 A2 | 7/2002 | |
| KR | 10-2010-0096823 A | 9/2010 | |
| KR | 20100096823 A * | 9/2010 | ............... H01R 4/20 |
| RU | 2082956 C1 | 6/1997 | |
| WO | 2016-030735 A1 | 3/2016 | |
| WO | 2017205723 A1 | 11/2017 | |

\* cited by examiner

MULTI-STAGE IRREVERSIBLE SENSOR COUPLING

BACKGROUND

The process measurement and control industry employs process variable transmitters to remotely monitor process variables associated with fluids such as slurries, liquids, vapors, gases in chemical, pulp, petroleum, pharmaceuticals, food and other processing plants. Examples of process variables include pressure, temperature, flow, level, turbidity, concentration, chemical composition, pH, gas detection and/or quantification, and other properties.

Process measurement systems employ sensors designed to sense a particular variable, such as temperature and employ measurement circuitry to sense or determine an electrical parameter of the sensor that can be used to calculate the process variable. For example, an RTD has a resistance that varies with temperature. Measurement circuitry coupled to an RTD may be configured to drive a small current through the RTD and measure a voltage across the RTD. The measured voltage is indicative of the resistance of the RTD and thus the temperature.

In another example, a gas detection system may employ an electrochemical sensor that provides an electrical response to the presence of a particular gas, such as hydrogen sulfide ($H_2S$). In such instances, the measurement circuitry provides a suitable electrical excitation to the gas detection sensor in order to measure or otherwise obtain a sensor response.

Thus, process measurement systems employ a wide variety of sensors coupled to suitable detection electronics. Further, in some instances, the sensor may also include sensor electronics, that may amplify, linearize, or otherwise process the sensor signal before providing it to higher order electronics of a process measurement system. Accordingly, in many process measurement systems, it is necessary to physically and electrically couple a sensor to sensor measurement electronics or higher order electronics of the process measurement system.

SUMMARY

A multi-stage irreversible sensor coupling is provided. A sensor body includes a sensor and has a sensor body wall and at least one sensor body engagement feature. A clip barrel is configured to slidably engage the sensor body and has at least one clip barrel engagement feature. A wedge clip is configured to slidably engage the clip barrel and has at least one wedge clip engagement feature that is configured to urge the at least one sensor body engagement feature into cooperative engagement with the at least one clip barrel engagement feature when the wedge clip, clip barrel, and sensor body are fully engaged together.

DETAILED DESCRIPTION OF ILLUSTRATIVE EMBODIMENTS

Some process measurement and control systems require a sensor body or module to be attached, both physically and electrically, to an electronics housing or module. While assembling the sensor body, it is often necessary to use an adhesive to permanently bond the final portions of the assembly. This permanent bond requires a controlled manufacturing process to ensure the quality of the adhesive joint. Oftentimes, this adds additional hour(s) and/or day(s) to the system build lead times. Additionally, the sensor is sometimes required to be tested on the final assembly line prior to application of the permanent adhesive and there is the possibility of the internal electrical connections between the sensor body and the electronics housing becoming damaged or otherwise corrupted due to operator handling of the adhesive process.

Embodiments described below generally provide a mechanical permanent coupling between a sensor body and an electronics housing that does not use permanent adhesive. Embodiments allow for partial assembly of the electrical end of the sensor body so that the electrical/signal connector that is being attached to the sensor can be wired and tested before finally coupling the connector into the sensor body at final assembly.

Figure 1:
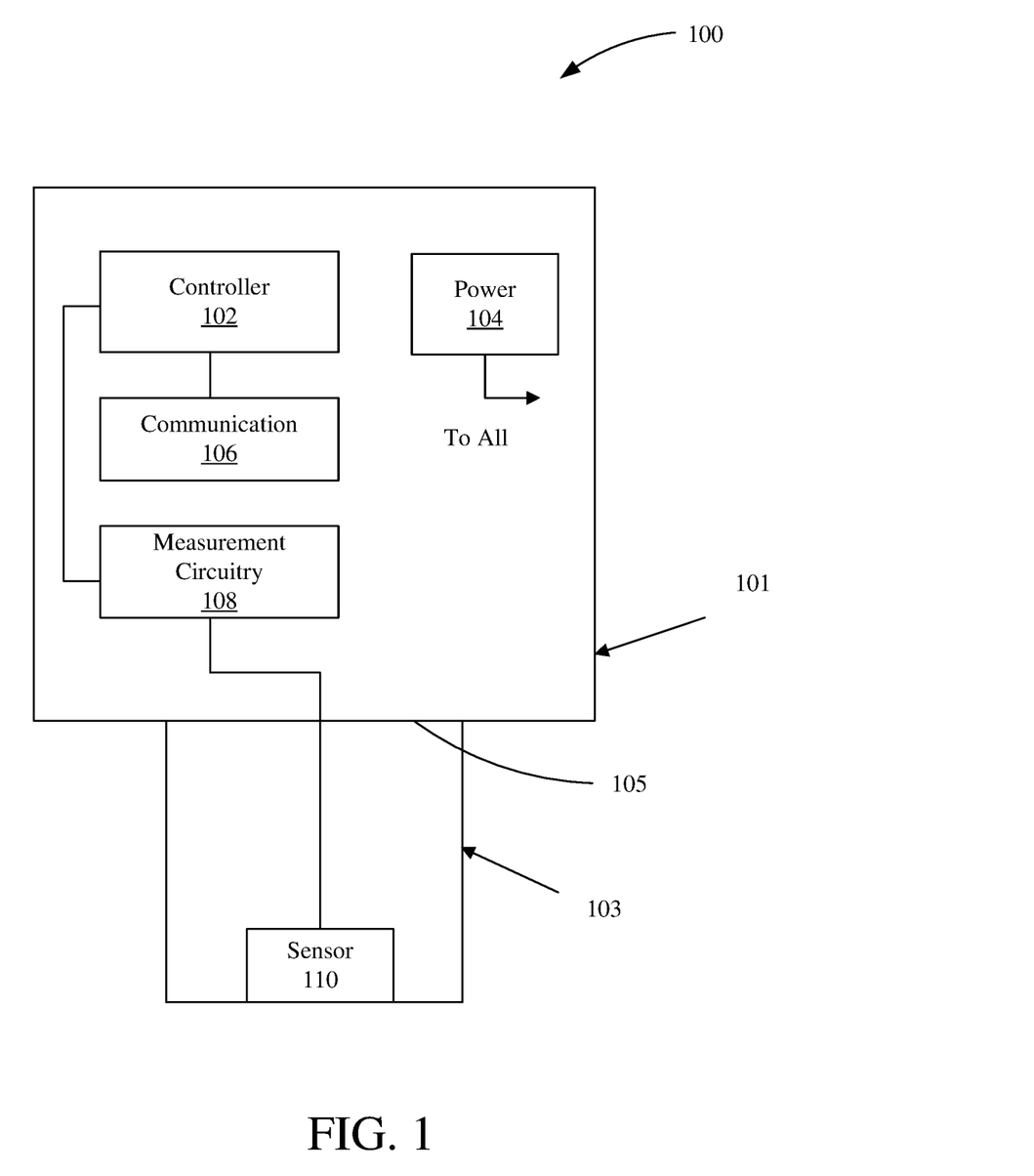
FIG. 1 is a block diagram of a process measurement system with which embodiments of the present invention are particularly useful.

FIG. 1 is a block diagram of a process measurement system with which embodiments of the present invention are particularly useful. Process measurement system 100 generally includes an electronics housing 101 coupled to a sensor body 103 at interface 105. Electronics housing 101 may include a controller 102 that is able to execute one or more programmatic steps in order to transform sensor signals received from measurement circuitry 108 into one or more process variable outputs. In some embodiments, controller 102 may be a microprocessor.

Electronics housing 101 may also contain power module 104 which is coupled to various subcomponents within system 100 as indicated by the arrow labeled "to all". In examples where the system is battery powered, power module 104 may include one or more batteries, either rechargeable or non-rechargeable, as well suitable power conditioning circuitry.

Controller 102 is coupled to communication circuitry 106, which may include any suitable circuitry that is able to convey information regarding the process variable output(s). Communication circuitry 106 allows controller 102 to communicate process variable information to the remote device, as indicated above, but also may allow the controller 102 to receive information from one or more remote devices. Suitable examples of such process communication include the 4-20 mA protocol, Highway Addressable Remote Transducer (HART®) Protocol, FOUNDATION™ Fieldbus Protocol, and the WirelessHART Protocol (IEC62591).

Measurement circuitry 108 includes any suitable circuitry for determining an electrical response of sensor 110. For example, measurement circuitry 108 may include voltage or current source and a suitable amplifier and analog-to-digital converter to read or otherwise interrogate an analog signal from sensor 110 and provide a digital indication thereof to controller 102.

Sensor 110 is disposed within sensor body 103 and has an electrical characteristic that varies with the process variable for which it is selected. For example, sensor 110 may be a temperature sensor or a pressure sensor. In other examples, sensor 110 may be a gas sensor, a pH sensor, a conductivity sensor, etc. Sensor body 103 is coupled to electronics housing 101 via a permanent coupling 105. Sensor 110 is electrically coupled to measurement circuitry 108 via permanent coupling 105.

Figure 2A:
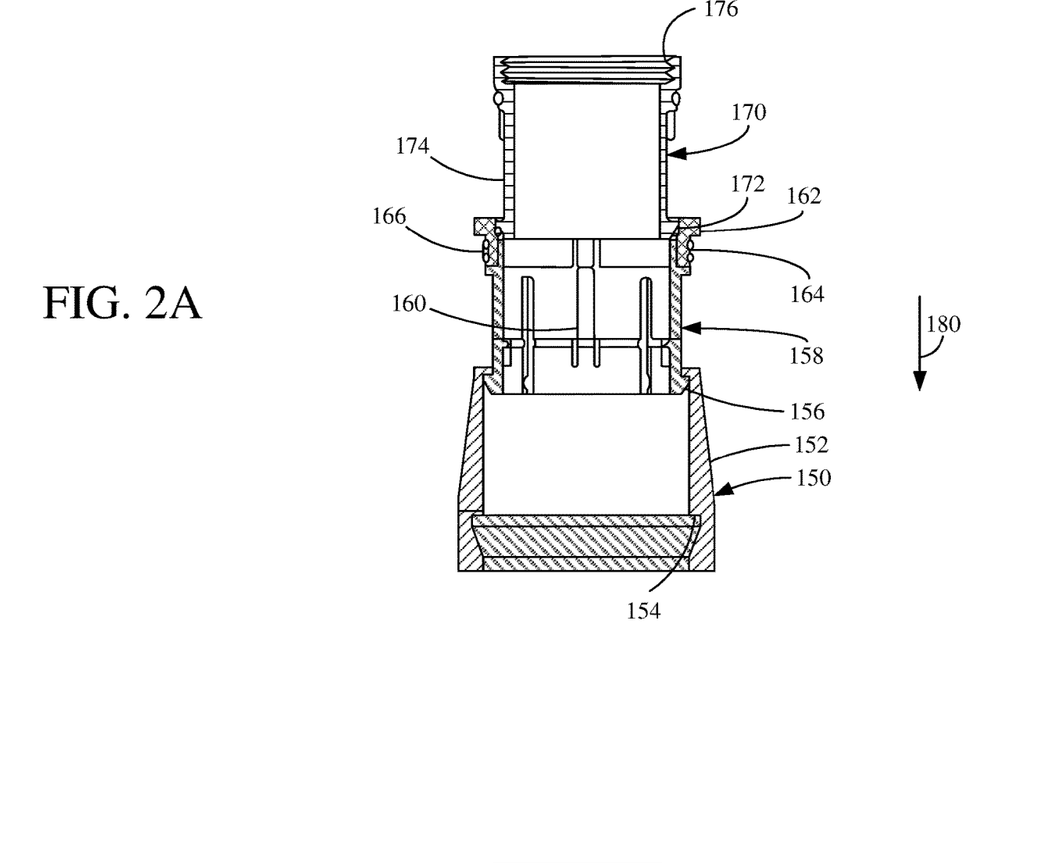
FIG. 2A is a diagrammatic cross-sectional view of a sensor body coupling in accordance with an embodiment of the present invention.

FIG. 2A is a diagrammatic cross-sectional view of a sensor body coupling in accordance with an embodiment of the present invention. A portion of sensor body is shown at reference numeral 150 and generally includes a substantially cylindrical sidewall 152 having an internal feature 154 that is configured to engage with a cooperative snap ring or fingers 156 on clip barrel 158. In the illustrated embodiment, feature 154 includes a recess 155 that is sized and shaped to receive fingers 156. Sensor body 150 may have any suitable number of electrical interconnect pins that engage cooperative pins of the electronics housing when the coupling is complete.

Clip barrel 158, in the illustrated example, includes one or more anti-rotation features 160, which will be described in greater detail below with respect to FIGS. 3 and 4. The anti-rotation features 160 ensure that clip barrel 158 may not be rotated with respect to sensor body 150 as the two components are coupled together. As shown, clip barrel 158 also generally includes a collar 162 having a shoulder portion 164 with a sealing ring, such as an O-ring, 166 disposed about shoulder portion 164. Wedge clip 170 is also shown having wedge clip interference feature 172 disposed at a distal end of sidewall 174. Sidewall 174 is generally cylindrical in shape and extends from interference feature 172 to a threaded engagement portion, illustrated as an internally threaded engagement portion 176.

Figure 2B:
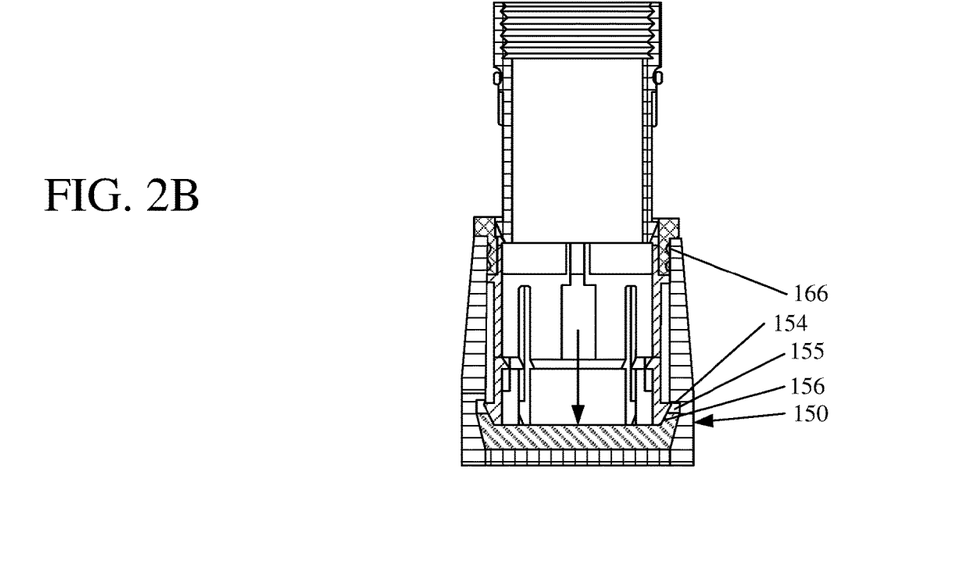
FIG. 2B is a diagrammatic view of a partially assembled sensor body coupling in accordance with an embodiment of the present invention.

During assembly, clip barrel 158 is first moved in the direction of arrow 180 with respect to sensor body 150. As this movement occurs, engagement feature 156 will be positioned near each other as illustrated in FIG. 2B. As can be seen, features 154, 156 are proximate one another but not yet engaged, and sealing ring 166 is sealing against an inner surface of sidewall 152 of sensor body 150.

Figure 2C:
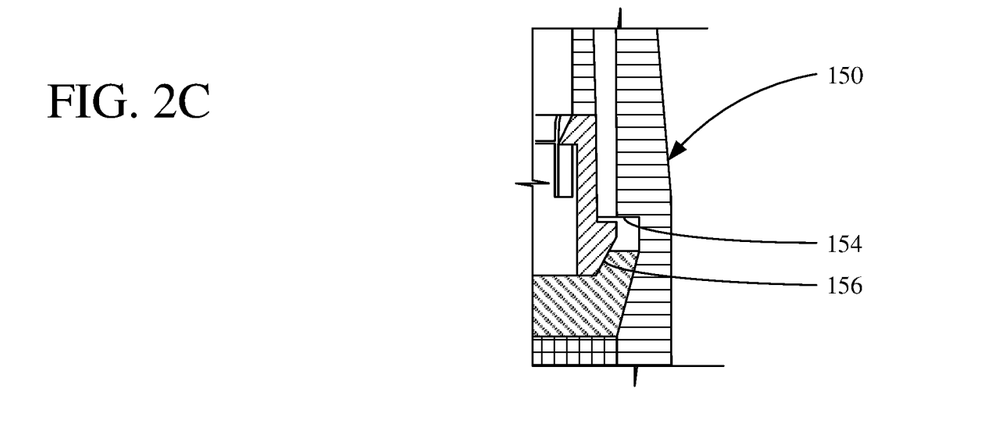
FIG. 2C is a diagrammatic view of a portion of a partially assembled sensor body coupling in accordance with an embodiment of the present invention.

FIG. 2C is an enlarged view of a portion of FIG. 2B showing cooperative features 154, 156 positioned proximate one another but not yet mechanically engaged together. Once features 154, 156 are positioned proximate one another, but not yet engaged together, step one of the coupling assembly is complete.

Figure 2D:
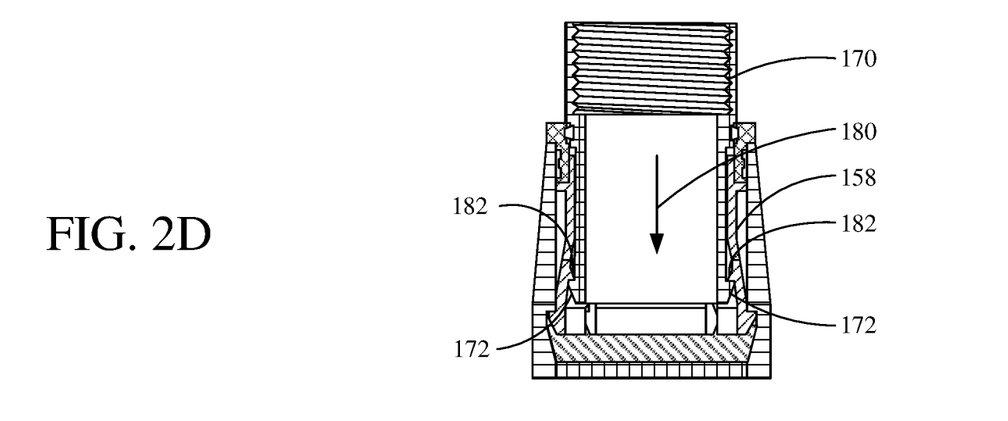
FIG. 2D is a diagrammatic view of an assembled sensor body coupling in accordance with an embodiment of the present invention.
Figure 2E:
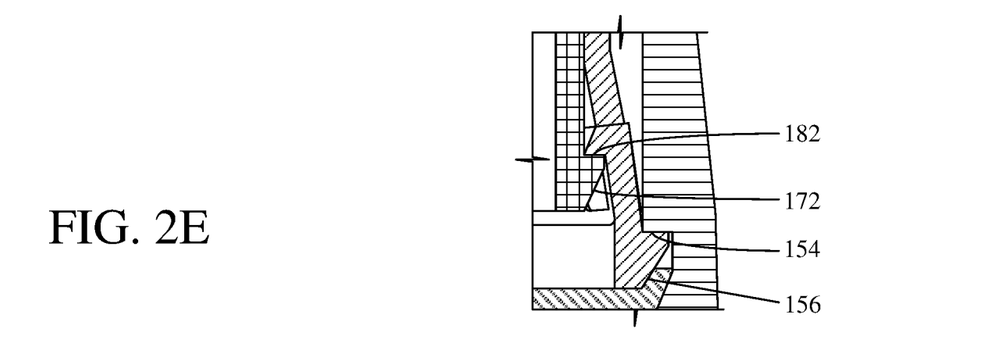
FIG. 2E is a diagrammatic view of a portion of a fully assembled sensor body coupling in accordance with an embodiment of the present invention.

FIG. 2D illustrates the completion of the second step of the coupling assembly. Specifically, wedge clip 170 is moved with respect to clip barrel 158 in the direction indicated by arrow 180. This movement occurs until end engagement features 172 of wedge clip 170 engage internal wedge portion 182 of clip barrel 158. The engagement of end engagement features 172 and internal wedge portion 182 cause cooperative features 154, 156 to become engaged, thereby completing the multi-step irreversible coupling of the sensor body. FIG. 2E is an enlarged view showing the completion of the two-step coupling operation with cooperative features 154, 156 engaged together and interference features 172 and 182 engaged together. At this point, a permanent mechanical coupling has been created that cannot be decoupled or removed without significantly damaging the clip barrel or wedge clip.

The two-step assembly process generally provides a wedge type connection that snaps together in a two-piece assembly. As set forth above, the clip barrel 158 and wedge clip 170 are arranged in a pre-assembled orientation shown in FIG. 2A. The clip barrel 158 is designed to slide into sensor body 150 without any interference as shown in FIGS. 2B and 2C. Clip barrel 158 has engagement features, such as hooked fingers that spread apart, engaging the groove of the sensor body, as shown in FIG. 2C. The sensor can then be final line tested to confirm a functioning sensor or calibrated or interacted with in any suitable way after this first step. Rework of faulty sensors is also possible at this point in the process. The insertion of the wedge clip 170 is the second step of the two-piece assembly. At this point, wedge clip 170 spreads the hooked fingers 156 of clip barrel 158. Wedge clip 170 also has features 172 that act as a wedge when engaged with clip barrel 158 thereby creating a permanent coupling, as shown in FIGS. 2D and 2E. The probability of connection corruption in the second step is low due to a single direction movement of components that can be designed for. While the coupling can be pulled apart with a large enough force, the design is meant to be rendered useless if this happens. Accordingly, the mechanical coupling is considered permanent. Such permanent couplings could help ensure that the assembly is tamper proof, which may be useful for various reasons.

Figure 3:
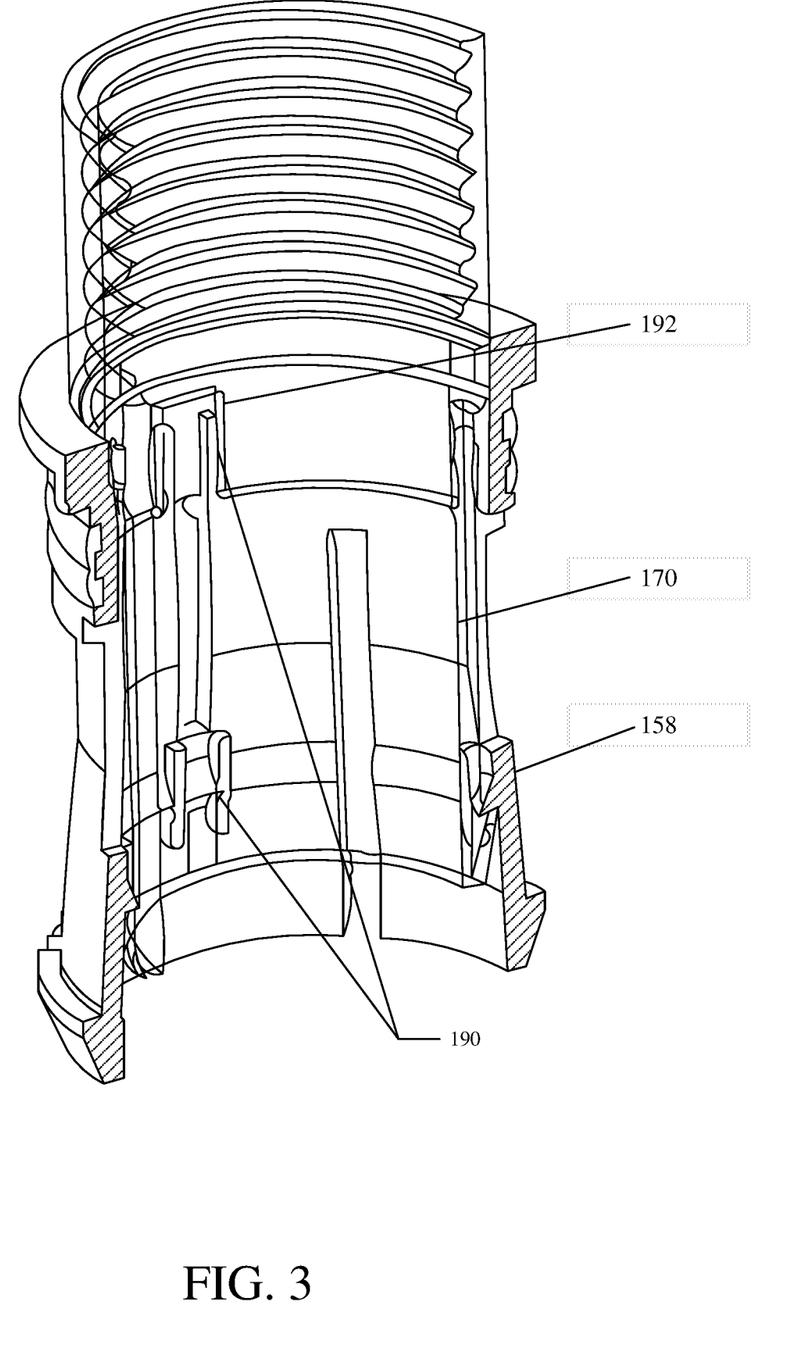
FIG. 3 is a diagrammatic cross-sectional perspective view of a portion of the clip barrel and wedge clip engaged together to illustrate one or more anti-rotation features in accordance with an embodiment of the present invention.

FIG. 3 is a diagrammatic cross-sectional perspective view of a portion of the clip barrel and wedge clip engaged together in order to illustrate one or more anti-rotation features in accordance with an embodiment of the present invention. As can be seen, one or more longitudinal anti-rotation cleats 190 extend inwardly from an inside surface of clip barrel 158. These cleats 190 are engaged by a suitable groove 192 of wedge clip 170. In this way, the wedge clip cannot rotate with respect to clip barrel 158 as wedge clip 170 is inserted axially into clip barrel 158.

Figure 4:
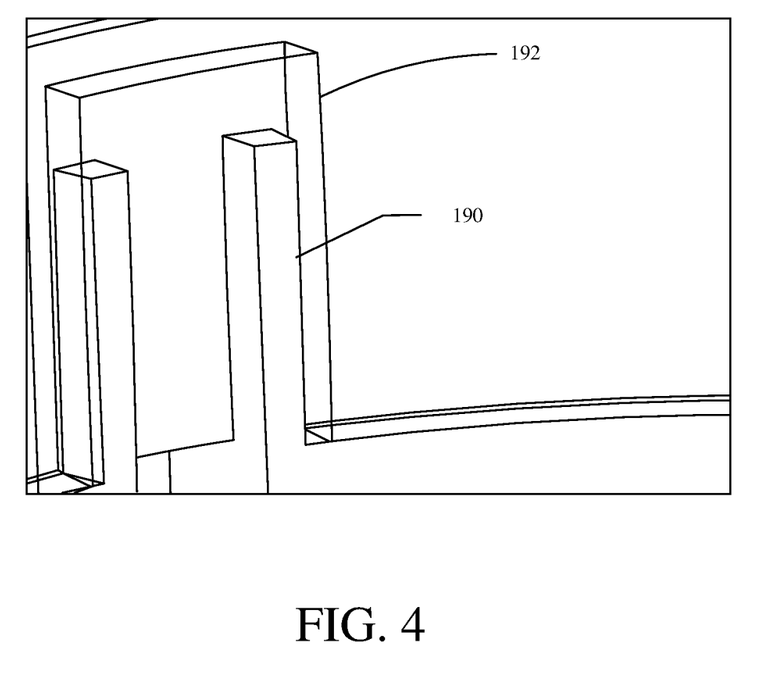
FIG. 4 is an enlarged diagrammatic view illustrating vertical cleats disposed within a channel in order to prevent rotation in accordance with an embodiment of the present invention.

FIG. 4 is an enlarged diagrammatic view illustrating vertical cleats 190 disposed within channel 192 in order to prevent rotation. These anti-rotation features help ensure that wires connected to the housing and potted circuit board do not twist and break free during the assembly process.

Figure 5:
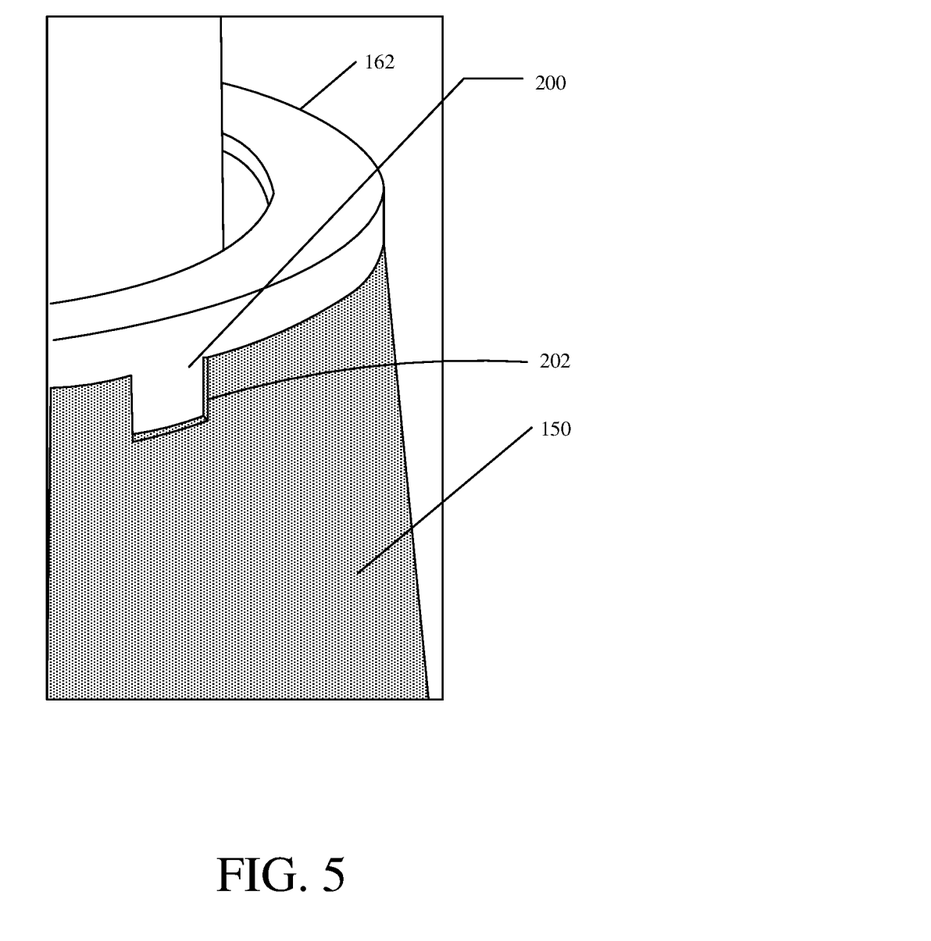
FIG. 5 is a diagrammatic view illustrating a collar of a clip barrel having an anti-rotation lock that engages within an anti-rotation groove of a sensor body in accordance with an embodiment of the present invention.

FIG. 5 is a diagrammatic view illustrating collar 162 of clip barrel 158 having an anti-rotation tab 200 that engages within an anti-rotation groove 202 of sensor body 150 when clip barrel 158 is engaged with sensor body 150.

While embodiments described thus far have generally shown specific mechanical features that provide snap engagement and/or anti-rotation, it is expressly contemplated that various cooperation can be reversed and/or alternate mechanical features can be used. For example, in the embodiment shown in FIG. 5, clip body 158 could include an anti-rotation groove or channel that is engaged by a tab on sensor body 150.

Figure 6:
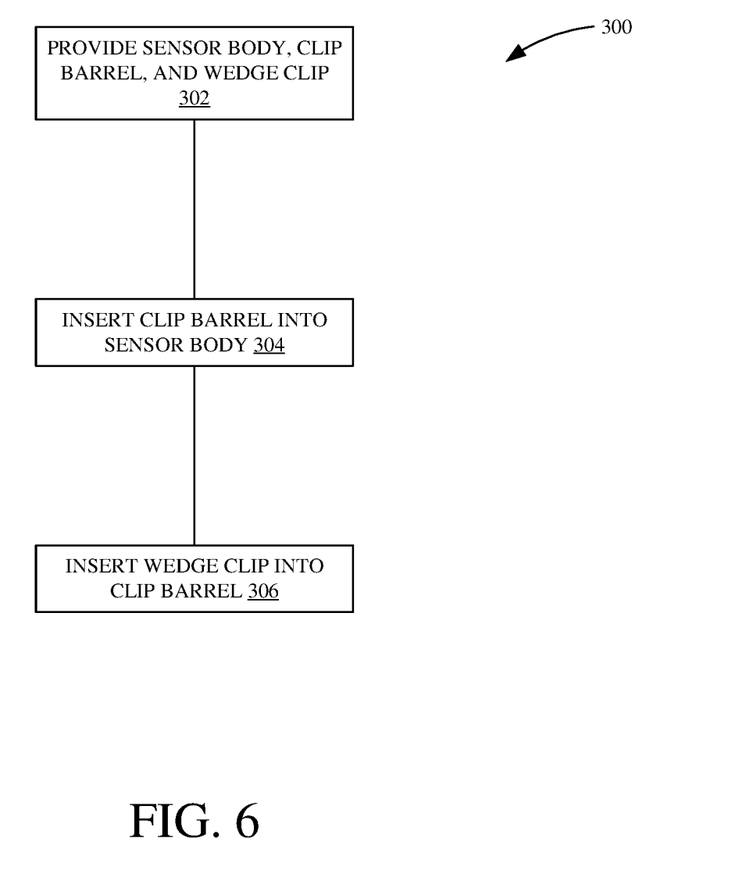
FIG. 6 is a flow diagram of a method of coupling sensor body to an electronics housing of a process measurement system in accordance with one embodiment.

FIG. 6 is a flow diagram of a method of coupling a sensor body to an electronics housing of a process measurement system in accordance with one embodiment. Method 300 begins at block 302 where a sensor body, a clip barrel, and a wedge clip are provided. Upon completion of the step indicated at block 302, an arrangement such as that shown in FIG. 2A is prepared. Next, at block 304, the clip barrel is inserted into the sensor body. Once this step is complete, the sensor may still be interacted with. For example, the sensor may still be tested to confirm a functioning sensor prior to finishing the permanent couple. Upon completion of step 304, an arrangement, such as that shown in FIG. 2B is provided. Next, at block 306, the wedge clip is inserted into the clip barrel. This finalizes a permanent mechanical coupling to the sensor body. Upon completion of step 306, an arrangement, such as that shown in FIG. 2D is provided. Preferably, steps 304 and 306 are done in purely axial motion, without generating any rotation with respect to the particular components whatsoever. Once the permanent mechanical coupling is completed, the coupling may be provided with molded or over-molded seals in order to prevent leaking to help replace the adhesive joint seal.

While embodiments described herein are applicable to components that use any suitable materials, it is expressly contemplated that embodiments could be practiced where a single part is molded where one portion could be half stainless steel, and the other portion could be half molded plastic. Alternatively, the single part could be produced strictly in stainless steel or any other suitable metal, or in strictly molded plastic, or any other suitable polymer. Finally, the size of the coupling may vary depending on the application.

Although the present invention has been described with reference to preferred embodiments, workers skilled in the art will recognize that changes may be made in form and detail without departing from the spirit and scope of the invention.

What is claimed is:

1. A multi-stage irreversible sensor coupling comprising:
a sensor body having a sensor, the sensor body having a sensor body wall and at least one sensor body engagement feature;
a clip barrel configured to slidably engage the sensor body, the clip barrel having a plurality of fingers, each finger having a wedge-shaped end that is configured to engage the at least one sensor body engagement feature; and
a wedge clip configured to slidably engage the clip barrel, the wedge clip having at least one wedge clip engagement feature that is configured to urge the plurality of fingers outwardly into cooperative engagement with the at least one sensor body engagement feature when the wedge clip, clip barrel, and sensor body are fully engaged together.

2. The multi-stage irreversible sensor coupling of claim 1, wherein the sensor body wall is cylindrical.

3. The multi-stage irreversible sensor coupling of claim 1, wherein the at least one sensor body engagement feature includes a recess that is configured to receive the wedge-shaped end of each finger of the plurality of fingers.

4. The multi-stage irreversible sensor coupling of claim 1, wherein at least one of the sensor body and the clip barrel are configured to prevent rotation between the sensor body and the clip barrel as the clip barrel slides relative to the sensor body.

5. The multi-stage irreversible sensor coupling of claim 1, wherein at least one of the clip barrel and the wedge clip are configured to prevent rotation between the clip barrel and the wedge clip as the wedge clip slides relative to the clip barrel.

6. The multi-stage irreversible sensor coupling of claim 1, wherein the sensor is selected from the group consisting of a temperature sensor, a pressure sensor, a gas sensor, a pH sensor, and a conductivity sensor.

7. The multi-stage irreversible sensor coupling of claim 1, wherein the at least one wedge clip engagement feature includes a wedge clip interference feature located at a distal end of the wedge clip, the at least one wedge clip engagement feature forming a wedge when engaged with the at least one clip barrel engagement feature.

8. The multi-stage irreversible sensor coupling of claim 1, wherein the wedge clip has a cylindrical sidewall configured to be slidably received within the clip barrel.

9. The multi-stage irreversible sensor coupling of claim 1, wherein the wedge clip includes a threaded portion disposed on an opposite end of the wedge clip from the at least one wedge clip engagement feature.

10. The multi-stage irreversible sensor coupling of claim 1, wherein the clip barrel includes a collar configured to abut the sensor body when the clip barrel and sensor body are fully engaged.

11. The multi-stage irreversible sensor coupling of claim 10, wherein the clip barrel includes a shoulder portion proximate the collar, the shoulder portion having a sealing element disposed thereabout.

12. The multi-state irreversible sensor coupling of claim 1, wherein the at least one wedge clip engagement feature includes a plurality of wedge clip engagement fingers, each finger having a wedge-shaped end that is configured to cooperate with an internal wedge portion of the clip barrel to maintain the wedge clip within the clip barrel.

* * * * *